United States Patent [19]

Bononi

[11] Patent Number: 5,104,893

[45] Date of Patent: Apr. 14, 1992

[54] IMIDAZOLE DERIVATIVES HAVING THERAPEUTICAL ACTIVITY, PROCESS FOR THEIR PREPARATION AND PHARMACEUTICAL COMPOSITIONS CONTAINING THEM

[75] Inventor: Loris J. Bononi, Gabbiana, Italy

[73] Assignee: Bononi & C. Gruppo di Ricera SrL, Firenze, Italy

[21] Appl. No.: 617,281

[22] Filed: Nov. 16, 1990

Related U.S. Application Data

[63] Continuation of Ser. No. 464,593, Jan. 12, 1990, abandoned, which is a continuation of Ser. No. 134,788, Dec. 18, 1987, abandoned.

[30] Foreign Application Priority Data

Dec. 19, 1986 [IT] Italy ................................ 22783 A/86

[51] Int. Cl.$^5$ .................. C07D 233/56; A61K 31/415
[52] U.S. Cl. ..................................... 514/399; 548/341
[58] Field of Search ......................... 548/341; 514/399

[56] References Cited

U.S. PATENT DOCUMENTS 4,657,923  4/1987  DiSchiena .......................... 514/399

OTHER PUBLICATIONS

Merck Index, Eighth Ed., Merck and Co., Rahway, N.J., 1968, pp. 1003-1004.
Chemical Abstracts, 103:193006h (1985) [Khadikar, P. et al., Indian J. Pharm. Sci. 1984, 46(6), 209-211].
Chemical Abstracts, 106:192587y (1987) [Khadikar, P. et al., Rev. Microbiol. 1986, 17(4), 291-295].

Primary Examiner—Mary C. Lee
Assistant Examiner—Lenora Miltenberger
Attorney, Agent, or Firm—Michael N. Meller

[57] ABSTRACT

The econazole and miconazole sulfosolicylic acid addition salts show, in vitro, a relevant anti-fungal activity with wide spectrum and, if locally applied, are well tolerated and more effective than the corresponding nitrates for the control, in vivo and clinically, of the mycosis as induced from dermatophytes and from candida albicans.

7 Claims, 6 Drawing Sheets

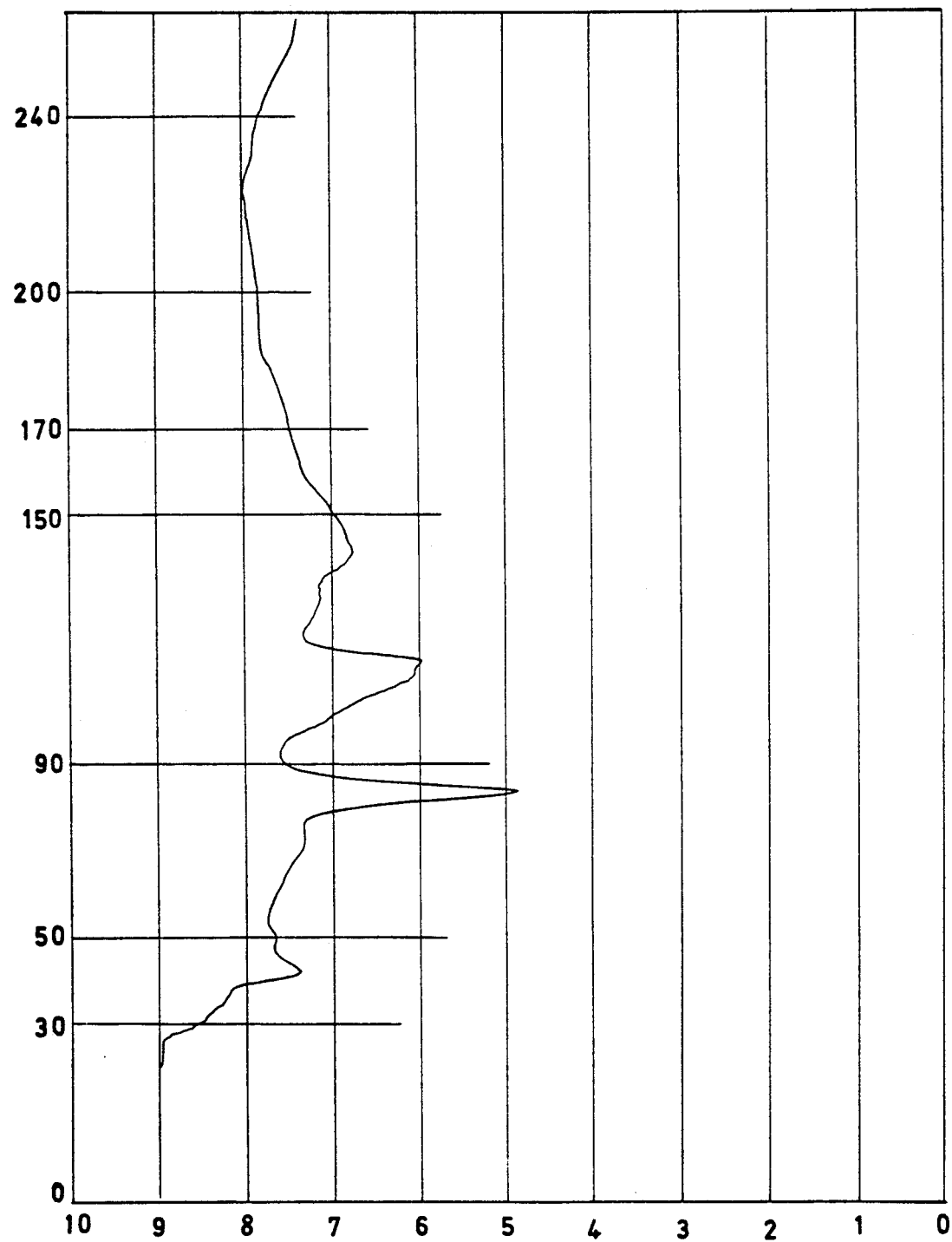

IMIDAZOLE DERIVATIVES HAVING THERAPEUTICAL ACTIVITY, PROCESS FOR THEIR PREPARATION AND PHARMACEUTICAL COMPOSITIONS CONTAINING THEM

This application is a continuation of application Ser. No. 07/464,593, filed 1/12/90 now abandoned, which is a continuation, of application Ser. No. 07/134,788, filed 12/18/87, now abandoned.

The present invention relates to novel imidazole derivatives, more specifically to two novel addition salts with sulphosalicylic acid of econazole, namely, 1-(2-((4-chlorophenyl)-methoxy)-2-(2,4-dichlorophenyl)-ethyl)-1-H-imidazole, and of miconazole, namely, 1-(2-((2,4-dichlorophenyl)-2-(2,4-dichlorophenyl)methoxy)-ethyl)-1H-imidazole, having therapeutical activity, particularly anti-mycotic activity.

The novel derivatives of the present invention have following general formula:

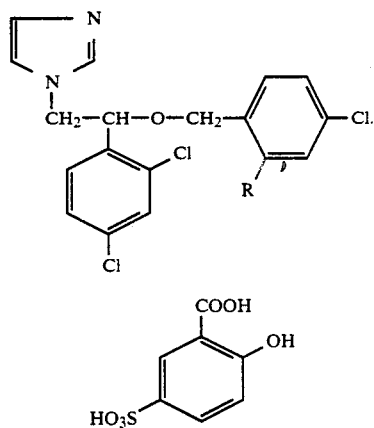

wherein R represents H or Cl.

The cutaneous mycoses are infections mainly induced from dermatophytes and from *Candida albicans*. The dermatophytes are fungi found as parasites in the horny layer, in the hair and in the nails owing to the presence of keratolitic enzymes, capable of hydrolyzing the long polypeptidic chains of keratin.

Three genuses (Trichophyton, Microsporum and Epidermophyton) are mainly responsible of the cutaneous pathologies. The infections induced from dermatophytes are generally defined as tinea. Depending on the part affected there are several clinical pictures: *tinea capitis, tinea barbae, tinea corporis, tinea cruris, tinea pedis, tinea manuum, tinea faciei,* and *tinea unguium.*

The *Candida albicans* is a ubiquitous non keratinophylic fungus, normally being a saprophyte of cutis and of mucosae, which becomes pathogenic when its sprouting and reproduction are promoted by a particularly suitable environment or by the weakening of the organic defences.

The clinical evidences induced from *Candida albicans* vary according to the part involved: intertriginis, vulvovaginities, oral candidiases ("thrush"), boccheruolo, and paronichia.

Among the drugs useful for the topical treatment of surface mucosae the imidazole derivatives have acquired, in the last years, a relevant importance.

More particularly the active principles known as econazole (DCI) and miconazole (DCI), correspond to the above indicated chemical names, are anti-mycotic drugs with a wide activity spectrum; they are endowed with a powerful activity against dermatophytes and *Candida albicans*, as well as against some gram-positive germs. Their action takes place by selective inhibition of the purine and glutamine fixing onto the membrane of mycetes.

The miconazole and the econazole are used as nitrates in several pharmaceutical forms (cream, powder, ovuli, etc.).

The imidazole compounds according to the present invention are chemically defined in the following manner:

a) 1-(2-((4-chlorophenyl)-methoxy)-2-(2,4-dichlorophenyl)-ethyl)-1H-imidazole 5-sulfosalicylate (econazole SSA) corresponding to the formula $C_{25}H_{20}Cl_4N_2O_7S$.

Its molecular weight is 599.89.

Its centesimal elemental analysis is the following: C 50.05 (found 50.25); H 3.53 (found 3.47); N 4.67 (found 4.81); O 18.67 (found 18.54); S 5.34 (found 5.49); Cl 17.74 (found 17.44, by difference).

The substance is in the form of a white fine powder, is soluble in methanol, ethanol and dimethylsulfoxide, poorly soluble in water, insoluble in the common organic solvents.

It crystallizes from methyl or ethyl alcohol and melts at 176°–178° C. (at Kofler).

The saturated aqueous solution of the salt has a pH of 3.15, as measured with a glass electrode.

b) 1-(2-(2,4-dichlorophenyl)-2-((2,4-dichlorophenyl)-methoxy)ethyl)-1H-imidazole 5-sulfosalicylate (miconazole SSA) corresponding to the formula $C_{25}H_{20}Cl_4N_2O_7S$.

Its molecular weight is 634.3.

Its centesimal elemental analysis is the following: C 47.34 (found 47.49); H 3.18 (found 3.32); N 4.42 (found 4.59); O 17.66 (found 17.51); S 5.05 (found 4.92); Cl 22.35 (found 22.17, by difference).

The substance is in the form of a white fine powder, is soluble in methanol, ethanol and DMSO, poorly soluble in water, insoluble in the common organic solvents. It crystallizes from ethyl or methyl alcohol and melts at 181°–183° C. (Kofler). The saturated aqueous solution of the salt has a pH of 3.20 as measured with a glass electrode.

The compounds according to the present invention are produced by reacting in ethanol solution under boiling miconazole and, respectively, econazole with 5-sulphosalicylic acid in equimolar proportions; the reaction mixture is concentrated to dryness, and thereafter the residue is taken up with ethyl ether and crystallized from ethyl alcohol. The process shall be better understood from the following examples, having purely illustrative and non limiting purposes.

BRIEF DESCRIPTION OF THE DRAWINGS

FIGS. 3–6 are ultraviolet, infrared and differential thermal analysis spectra, respectively, of econazole 5-sulfosalicylate.

EXAMPLE 1

1.82 g of 5-sulfosalicylic acid (7.2 mmoles) were dissolved at room temperature in 40 ml of absolute ethyl alcohol. Then 3 g of miconazole base (7.2 mmoles) were added, it being likewise known as 1-(2-((2,4-dichlorophenyl)-2-(2-(2,4-dichlorophenyl)methoxy)ethyl)-1H-imidazole, and the mixture was refluxed.

After complete solubilization of the miconazole, the solution was maintained under refluxing for 10 minutes, then it was charged in a rotating evaporator under vacuum, and concentrated to dryness in the water bath of the apparatus. The residue was taken up with ethyl ether, the mixture being cooled from outside with a refrigerating mixture, filtered under vacuum and crystallized from ethyl alcohol. In this way with a quantitative yield of the final product was obtained, it having the appearance of a white powder having melting point 181°-183° C. (Kofler).

Figure 1:
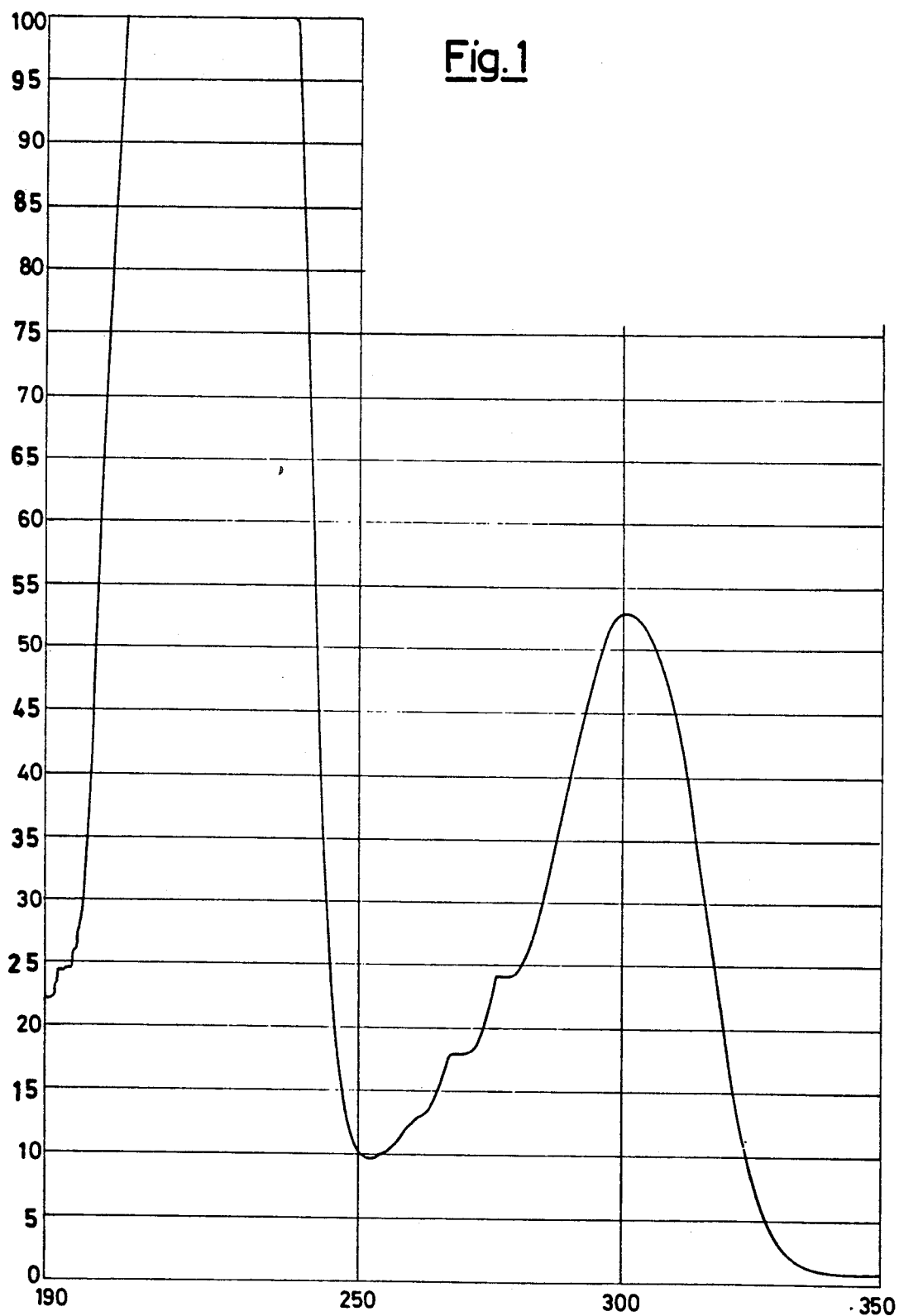
FIGS. 1 and 2 are ultraviolet and infrared spectra respectively, of miconazole 5-sulfosalicylate.
Figure 2:
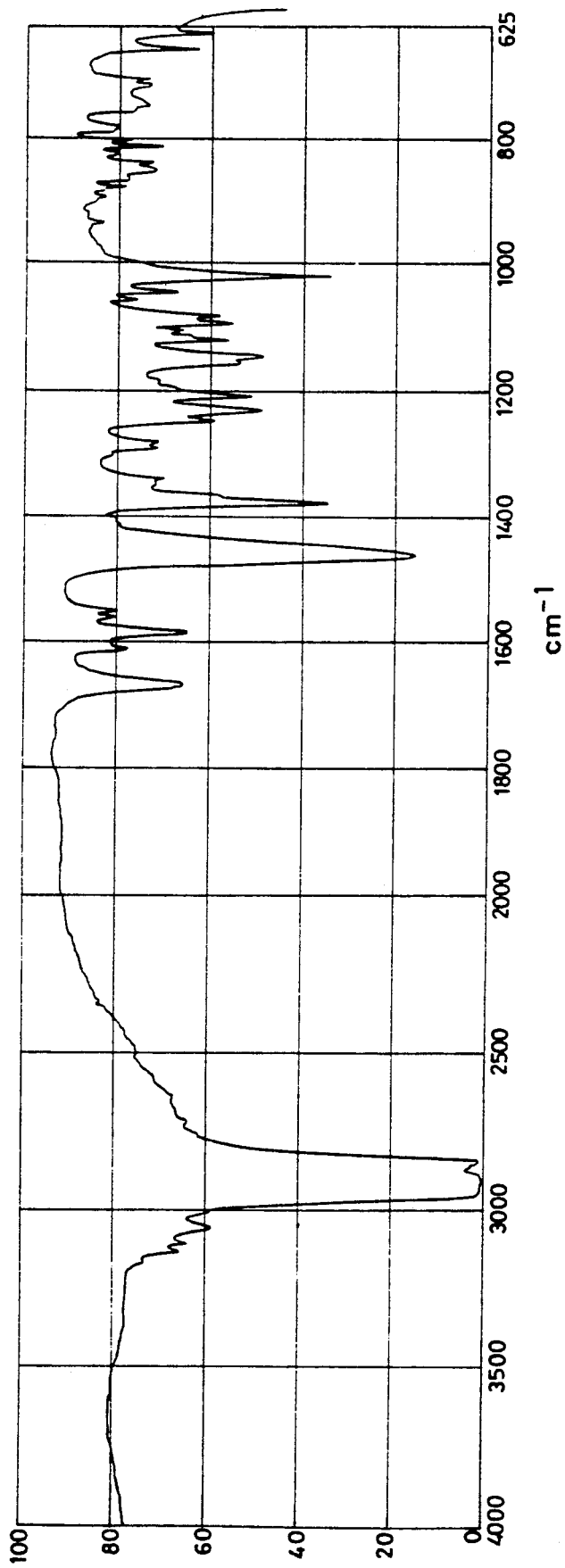
Figure 3:
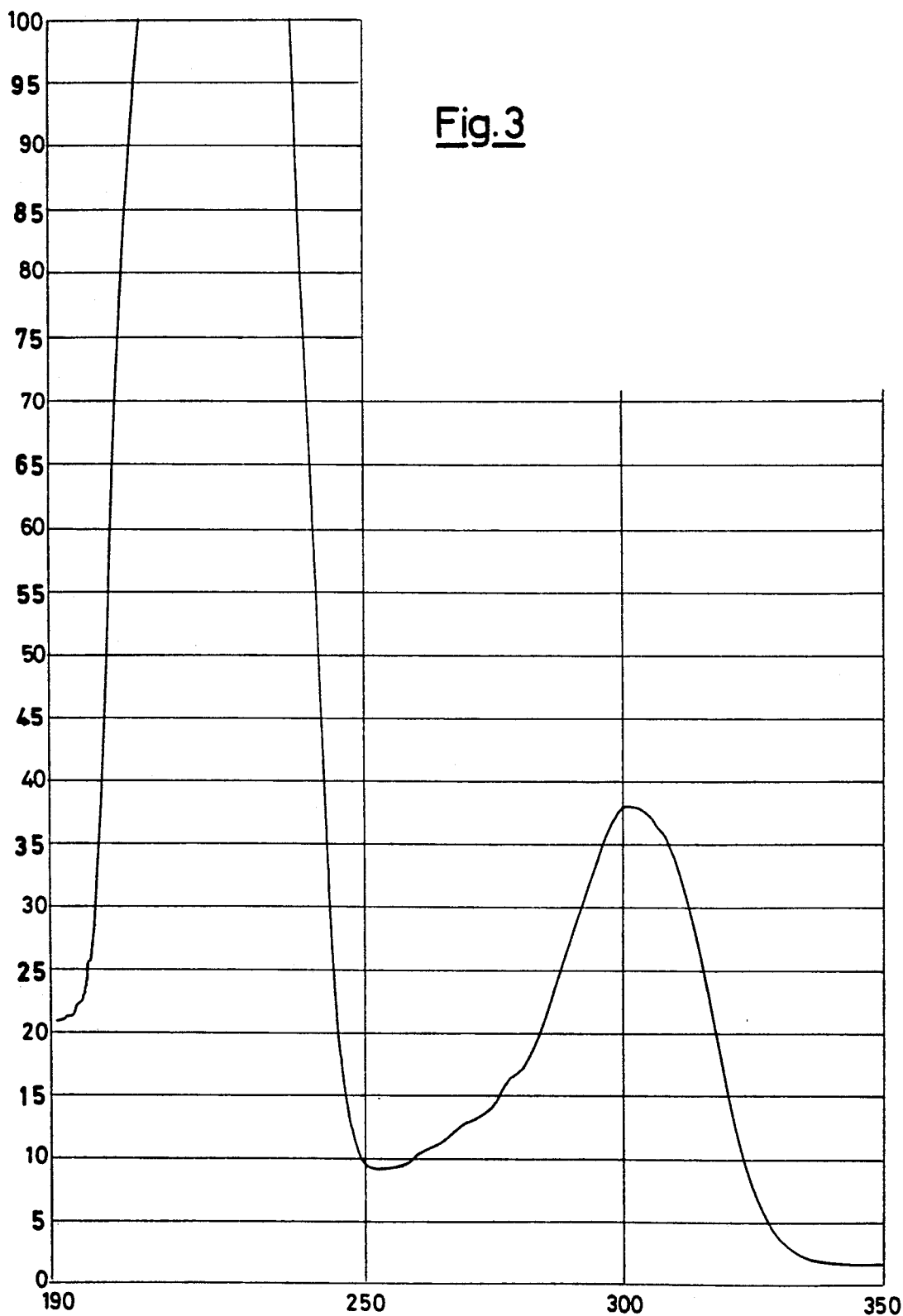
Figure 4:
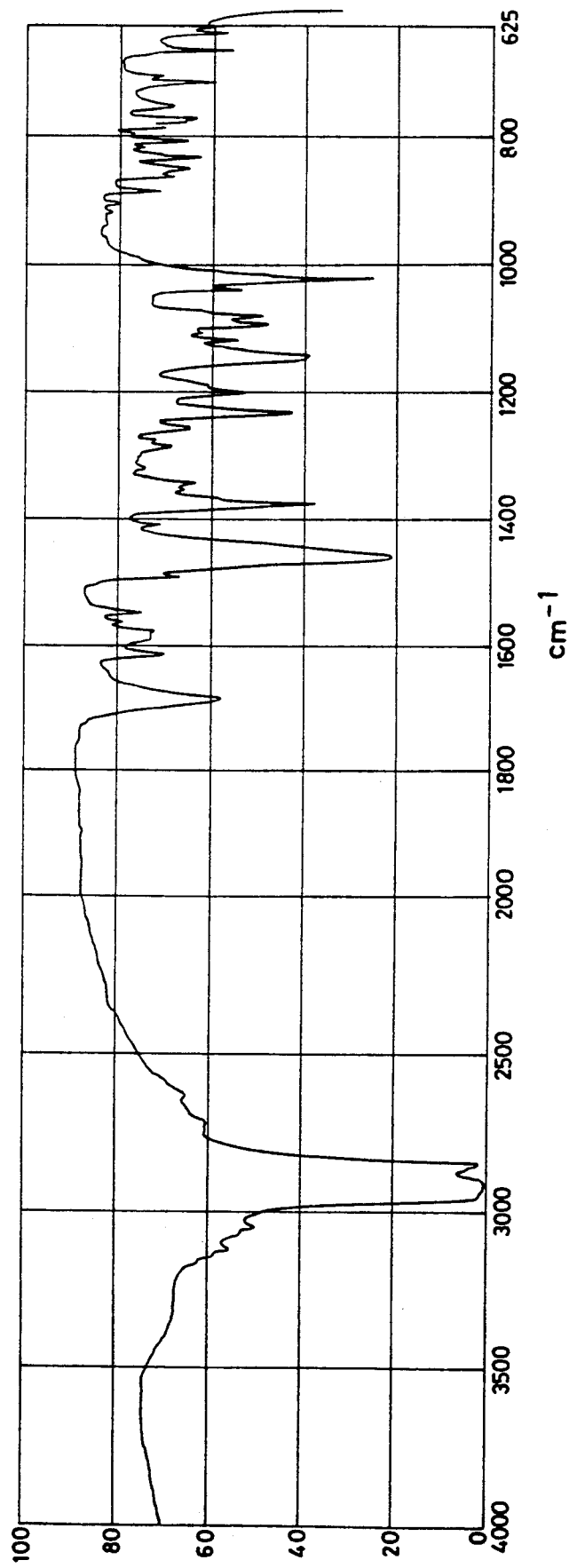
Figure 5:
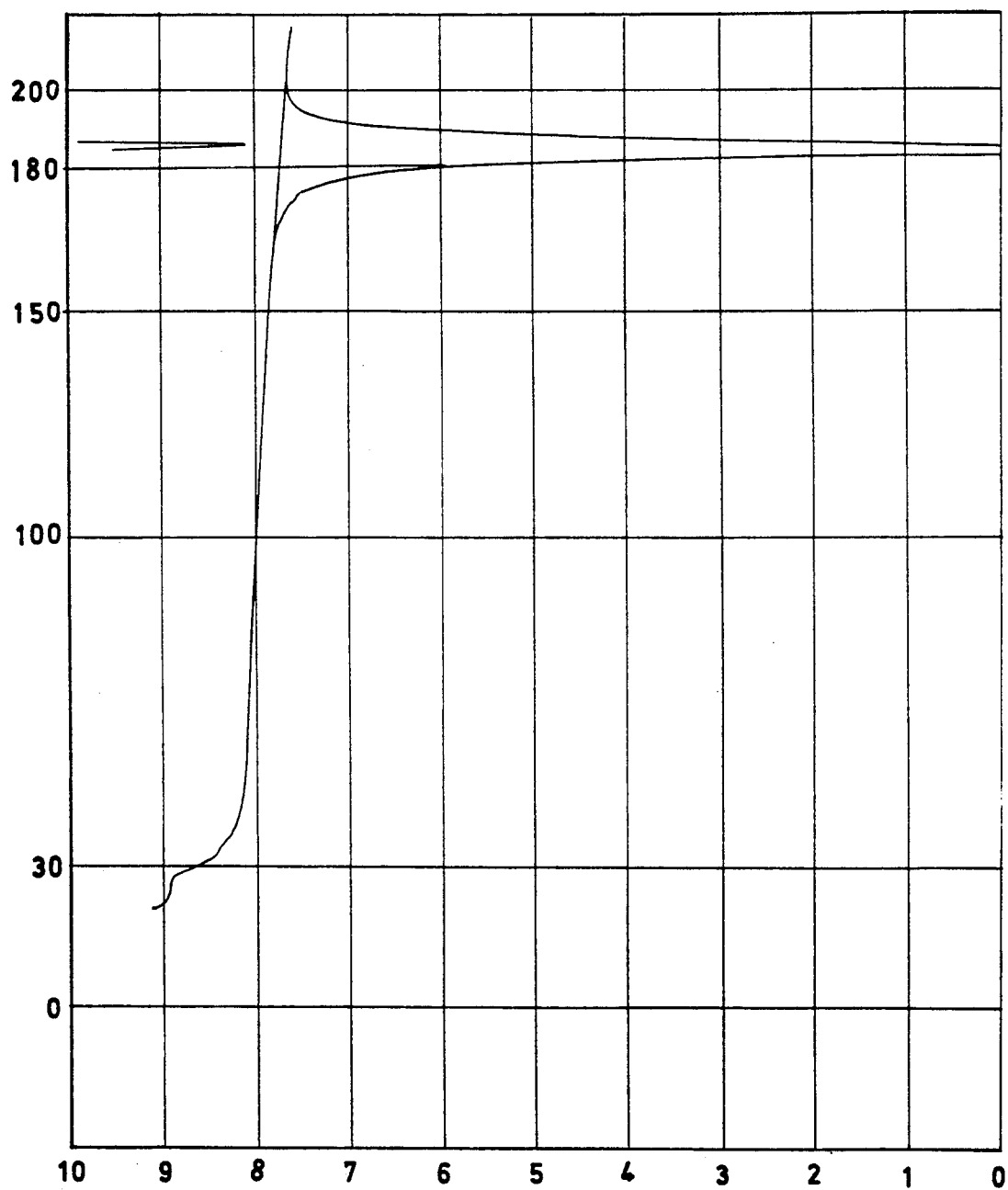

The UV and IR spectra confirm the foreseen structure (FIGS. 1-2).

EXAMPLE 2

1.98 g of 5-sulfosalicylic acid (7.8 mmoles) were dissolved at room temperature in about 40 ml of absolute ethyl alcohol. Then 3 g of econazole base (7.8 mmoles), also known as 1-(2-((4-chlorophenyl)-methoxy-2-(2,4-dichlorophenyl)-ethyl)-1H-imidazole, were added and the mixture was refluxed. After complete solubilization of the econazole, the solution was maintained at refluxing for 10 minutes; then it was placed into a rotating evaporator under vacuum and concentrated to dryness in the water bath of the apparatus.

The residue was taken up with ethyl ether by cooling it from outside with a refrigerating mixture, filtered under vacuum and crystallized from ethyl alcohol.

In this manner there was obtained, with quantitative yields, the final product having the appearance of a white fine powder and having a melting point of 176°-178° C. (Kofler).

The UV and IR spectra and the differential thermal analysis have confirmed the foreseen structure (FIG. 3-6).

The compounds of the present invention were the subject of pharmacological investigation, both in vitro and in vivo, the results of which, for reporting clarity, shall be separately illustrated for each compound.

I-a In vitro Antimycotic Activity

The antimycotic activity of miconazole SSA was been evaluated against *Candida albicans* 73/079 (YMA and SAB), *Cryptococcus neoformans* 451, *Saccharomyces cerevisiae*, *Aspergillus niger*, *Trichophyton mentagrophyties* 569A, *Hendersonula toruloidea* TH65 and *Pacilomyces varioti*.

The microorganisms were incubated onto agar-glucose medium, (Sabourauds medium) at 30° or 37° C., depending on the species, in the presence of miconazole SSA.

The incubation was of 24 hours for *Candida* and *Cryptococcus*, of 48-72 hours for the other mycetes. The miconazole SSA was solubilized in dimethylsulfoxide (DMSO), and then diluted in phosphate buffer at pH 6.6 up to a concentration of 100 μg/ml.

The diameters of the inhibition areas are reported in table 1.

Under these experimental conditions the results indicate a relevant anti-mycotic activity in vitro of miconazole SSA.

Since for some imidazole derivatives a discrepancy has been detected, sometimes of relevant magnitude, between the antimycotic activity in vitro and that in vivo (Richardson et al., Antimicrob Agents Chemother 27: 832, 1985), and since both the tests of antimycotic activity in vivo and the tests of therapeutical activity in the human being suffering from skin mycosis are considered as more reliable than those in vitro (Odds et al. J. Antimicrob. Chemoter. 18, 473, 1986), the antimycotic activity of miconazole SSA has been controlled both in the experimental animals and in the human being.

I-b Antimycotic Activity in vivo

The antimycotic activity of miconazole SSA was investigated in vivo in an infection model induced from *Candida albicans* in comparison with miconazole nitrate.

The experiment was carried out according to the model of Van Cutsem and Thienpont (J. Van Cutsem and D. Thienpont. Experimental cutaneous *Candida albicans* infections in guinea pigs. Sabouraudia 9: 17, 1971).

A group of 40 guinea pigs, previously treated with alloxan, were inoculated with $3 \times 10^6$ blastospores and *C. albicans* in a shaved cutis area. The hair was shaved at beginning of the experiment and, subsequently, every seven days.

Immediately after the inoculation, the animals have been divided into four groups: the first group did not receive any treatment and was used as the control; the second group was treated with a placebo; the third group was treated with 2% miconazole nitrate cream; the fourth group was treated with 2% miconazole SSA cream. All the treatments have been carried out with two cutaneous applications per day at 12 hours interval between them.

The lesion entity has been evaluated after 7, 15 and 25 days from the inoculation according to a rating score scale: 0) no lesions; 1) slight lesion; 2) moderate lesion; 3) marked lesion; 4) heavy lesion.

The results are reported in table 2.

The placebo application (cream devoid of the active principle) had no influence on the lesion behaviour, as demonstrated from the possibility of superimposing the scores of the first group (no treatment) and of the second group of animals (placebo).

On the contrary, relevant slighter lesions and a quick recovery were observed in animals treated in comparison with 2% miconazole nitrate cream, as demonstrated from the lower score recorded for the third group at each of the three observations times.

Lastly, for the animals treated with 2% miconazole SSA cream a relevantly faster recovery was observed with respect to the animals treated with 2% miconazole nitrate cream, as demonstrated from difference of the scores recorded for the third and fourth groups of animals.

The results of the experiments demonstrated that miconazole SSA is endowed with an in vivo antimycotic activity higher than that of miconazole nitrate, thus leading to the recovery from the lesion induced by *Candida albicans* in shorter times and in a more efficacious way.

I-c Anti-Mycotic Activity in the Human Being

The antimycotic activity of miconazole SSA in the human being was evaluated in comparison with miconazole nitrate in the case of 20 patients suffering from vulvo vaginalis candidiasis, diagnostically assessed by means of cultural and microscopical examination.

The patients were randomized and treated, 10 with miconazole nitrate and 10 with miconazole SSA, in form of vaginal ovuli, each containing the equivalent of 100 mg of miconazole base. The posology was of 2 ovuli per day for 14 days. The cultural and microscopic examinations were repeated after 7 and 14 days from the beginning of the treatment and the results have been recorded and reported in the table 3.

From the results of clinical experiments a greater therapeutical effectiveness of the miconazole SSA with respect to the miconazole nitrate is shown as evidenced from the percentages of positivity at the culture examination (10 vs 40% at the seventh day; 0 vs 10% at 14° day (p<0.01) and at the microscopical examination for Candida albicans (10 vs 30% at 7° days; 0 vs 20% at 14° days) (p<0.01).

TABLE 1

Diameter of the inhibition area for some microorganisms in the presence of miconazole SSA and miconazole nitrate.

| Microorganism | M.S. mm | M.N. mm |
|---|---|---|
| Candida Albicans 73/079 (YMA) | 23.5 | 23.8 |
| Candida Albicans 73/079 (SAB) | 25.4 | 20.0 |
| Cryptococcus 451 | 22.4 | 30.4 |
| Saccharomyces cer. | 30.0 | 24.9 |
| Aspergillus niger | 22.1 | 17.0 |
| Trychopyton 569A | 43.9 | 31.4 |
| Hendersonula toruloidea TH65 | 19.2 | 23.1 |

M.S. = miconazole SSA
M.N. = miconazole nitrate

TABLE 2

Antimycotic activity of miconazole SSA in comparison with miconazole nitrate in a cutaneous infection model induced from Candida Albicans.

| Group | N. of guinea pigs | t (days) | Lesions scores 0 | 1 | 2 | 3 | 4 |
|---|---|---|---|---|---|---|---|
| No treatment | 10 | 7 | 0 | 0 | 1 | 4 | 5 |
|  |  | 15 | 0 | 0 | 1 | 5 | 4 |
|  |  | 25 | 0 | 2 | 2 | 3 | 3 |
| Placebo | 10 | 7 | 0 | 0 | 2 | 4 | 4 |
|  |  | 15 | 0 | 0 | 3 | 4 | 3 |
|  |  | 25 | 0 | 1 | 3 | 3 | 3 |
| Miconazole nitrate 2% | 10 | 7 | 1 | 3 | 4 | 2 | 0 |
|  |  | 15 | 4 | 3 | 2 | 1 | 0 |
|  |  | 25 | 7 | 3 | 0 | 0 | 0 |
| Miconazole SSA 2% | 10 | 7 | 3 | 3 | 4 | 0 | 0 |
|  |  | 15 | 6 | 3 | 1 | 0 | 0 |
|  |  | 25 | 8 | 2 | 0 | 0 | 0 |

Scores of the lesions:
0 absent;
1 slight;
2 moderate;
3 marked;
4 heavy.

TABLE 3

Antimycotic activity of miconazole SSA and miconazole nitrate in women suffering from vulvovaginalis candidiasis.

| | Treatment days | | |
|---|---|---|---|
| | 0 | 7 | 14 |
| (a) Percentage of positivity at culture examination for Candida Albicans | | | |
| Miconazole nitrate | 100 | 40 | 10 |
| Miconazole SSA | 100 | 10 | 0 |
| (b) Percentage of positivity at microscopical examination for Candida Albicans | | | |
| Miconazole nitrate | 100 | 30 | 20 |
| Miconazole SSA | 100 | 10 | 0 |

II-a In vitro Antimycotic Activity

The antimycotic activity of econazole SSA has been evaluated against Candida albicans 73/079 (YMA and SAB), Cryptococcus neoformans 451, Saccharomyces cerevisiae, Aspergillus niger, Trichophyton mentagrophytes 569A, Hendersonula toruloidea TH65 and Pacilomyces varioti.

The microorganisms were incubated onto agar-glucose medium, (Sabourauds medium) at 30° or 37° C., depending on the species, in the presence of econazole SSA.

The incubation was for 24 hours for Candida and Cryptococcus, and for 48-72 hours for the other mycetes. The econazole SSA has been solubilized in dimethylsulfoxide (DMSO), and then diluted in phosphate buffer at pH 6.6 up to a concentration of 100 µg/ml.

The diameters of the inhibition areas are reported in table 1.

Under these experimental conditions the results indicate a relevant anti-mycotic activity in vitro of econazole SSA.

Since for some imidazole derivatives a discrepancy has been detected, sometimes of relevant magnitude, between the antimycotic activity in vitro and that in vivo (Richardson et al., Antimicrob Agents Chemother 27: 832, 1985), and since both the tests of antimycotic activity in vivo and the tests of therapeutical activity in the human beings suffering from skin mycosis, are considered as more reliable than those in vitro (Odds et al. J. Antimicrob. Chemoter. 18, 473, 1986) the antimycotic activity of econazole SSA has been controlled both in the experimental animals and in the human beings.

I-b Antimycotic Activity in vivo

The antimycotic activity of econazole SSA has been investigated in vivo in an infection model induced from Candida albicans in comparison with econazole nitrate.

The experiment has been carried out according to the model of Van Cutsem and Thienpont (J. Van Cutsem and D. Thienpont. Experimental cutaneous Candida albicans infections in guinea pig. Sabouraudia 9: 17, 1971).

A group of 40 guinea pigs, previously treated with alloxan, has been inoculated with $3 \times 10^6$ boastospores and C. albicans in a shaved cutis area. The hair has been shaved at beginning of the experiment and, subsequently, every seven days.

Immediately after the inoculation, the animals were divided into four groups: the first group did not receive any treatment and was used as the control; the second group was treated with a placebo; the third group was treated with 2% econazole nitrate cream; the fourth group was treated with 2% econazole SSA cream. All the treatments were carried out with two cutaneous applications per day at 12 hour intervals between them.

The lesion entity was evaluated at 7, 15 and 25 days from the inoculation according to a rating scale: 0) no lesions; 1) slight lesion; 2) moderate lesion; 3) marked lesion; 4) heavy lesion.

The results are reported in table 2.

The placebo application (cream devoid of the active principle) had no influence on the lesion behaviour, as demonstrated by the possibility of superimposing the scores of the first group (no treatment) and of the second group of animals (placebo).

On the contrary, relevant slighter lesions and a quick recovery were observed in animals treated with 2% econazole nitrate cream, as demonstrated by the lower scores recorded for the third group at each of the three observations times.

Lastly, for the animals treated with 2% econazole SSA cream a relevantly faster recovery was observed with respect to the animals treated with 2% econazole nitrate cream, as demonstrated from the difference of the scores recorded for the third and fourth groups of animals.

The results of the experiments demonstrated that econazole SSA is endowed with an in vivo anti-mycotic activity higher than that of econazole nitrate, thus leading to the recovery of the lesion induced from *Candida albicans* in shorter times and in a more efficacious way.

I-c Anti-mycotic Activity in the Human Being

The antimycotic activity of econazole SSA in the human being has been evaluated in comparison with econazole nitrate in the case of 20 patients suffering from vulvovaginalis candidiasis, assessed by means of cultural and microscopical examination.

The patients have been randomized and treated, 10 with econazole nitrate and 10 with econazole SSA, in form of vaginal ovuli, each containing the equivalent of 100 mg of econazole base. The posology was of 2 ovuli per day for 14 days. The cultural and microscopic examinations were repeated after 7 and 14 days from the beginning of the treatment and the results have been recorded and reported in the table 6.

From the results of the clinical experiments a greater therapeutical effectiveness of the econazole SSA with respect to the econazole nitrate is shown as evidenced from percentages of positivity at the culture examination (10 vs 40% at the seventh day; 0 vs 10% at 14° day) ($p<0.01$) and at the microscopical examination for *Candida albicans* (10 vs 30% at 7° days; 0 vs 20% at 14° days) ($p<0.01$).

TABLE 4

Diameter of the inhibition area for some microorganisms in the presence of econazole SSA and econazole nitrate (100 µg/ml)

| Microorganism | E.S. mm | E.N. mm |
| --- | --- | --- |
| Candida Albicans 73/079 (YMA) | 27.3 | 23.8 |
| Candida Albicans 73/079 (SAB) | 23.4 | 20.0 |
| Cryptococcus 451 | 25.3 | 30.4 |
| Saccharomyces cer. | 31.6 | 24.9 |
| Aspergillus niger | 29.4 | 17.0 |
| Trychophton 569A | 45.1 | 31.4 |
| Hendersonula TH65 | 33.9 | 23.1 |
| Paecilomyces | 16.2 | 12.5 |

E.S. = econazole SSA
E.N. = econazole nitrate of econazole SSA and econazole nitrate (100 µg/ml)

TABLE 5

Antimycotic activity of econazole SSA in comparison with econazole nitrate in a cutaneous infection model induced from *Candida Albicans*.

| Group | N. of guinea pigs | t (days) | \multicolumn{5}{c}{Lesion scores} |||||
| --- | --- | --- | --- | --- | --- | --- | --- |
|  |  |  | 0 | 1 | 2 | 3 | 4 |
| No treatment | 10 | 7 | 0 | 0 | 1 | 5 | 4 |
|  |  | 15 | 0 | 0 | 1 | 4 | 5 |
|  |  | 25 | 0 | 2 | 3 | 2 | 3 |
| Placebo | 10 | 7 | 0 | 0 | 1 | 5 | 4 |
|  |  | 15 | 0 | 0 | 3 | 3 | 4 |
|  |  | 25 | 0 | 2 | 2 | 3 | 3 |
| Econazole nitrate 2% | 10 | 7 | 1 | 4 | 3 | 2 | 0 |
|  |  | 15 | 4 | 2 | 3 | 1 | 0 |
|  |  | 25 | 6 | 3 | 1 | 0 | 0 |
| Econazole SSA 2% | 10 | 7 | 3 | 3 | 4 | 0 | 0 |
|  |  | 15 | 6 | 3 | 1 | 0 | 0 |
|  |  | 25 | 8 | 2 | 0 | 0 | 0 |

Scores of the lesions:
0 absent;
1 slight;
2 moderate;
3 marked;
4 heavy.

TABLE 6

Antimycotic activity of econazole SSA and econazole nitrate in women suffering from vulvovaginalis candidiasis.

| | \multicolumn{3}{c}{Treatment days} |||
| --- | --- | --- | --- |
| | 0 | 7 | 14 |
| (a) Percentage of positivity at culture examination for *Candida albicans* ||||
| Econazole nitrate | 100 | 50 | 20 |
| Econazole SSA | 100 | 20 | 0 |
| (b) Percentage of positivity at microscopical examination for *Candida albicans* ||||
| Econazole nitrate | 100 | 40 | 10 |
| Econazole SSA | 100 | 20 | 0 |

The compounds of the present invention are used for the preparation of pharmaceutical forms suitable for the topical use and thus for the foreseen therapeutical application, such as creams, ointments, lotions gels, milk, tinctures, powders, ovuli, foams, vaginal capsules, vaginal washings, oral gels.

For their preparation the normal excipients, solvents, vehicles and additives are used, according to the standard pharmaceutical techniques.

As regards the dosage of the active principle in the aforesaid pharmaceutical formulations and as regards the use posology, the dosage and posology already known and used for the corresponding nitrates still hold true.

I claim:
1. An imidazole compound having the formula:

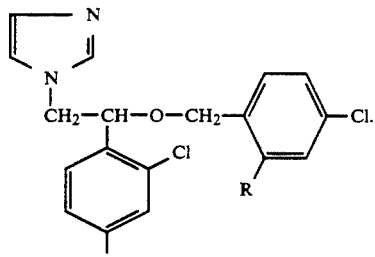

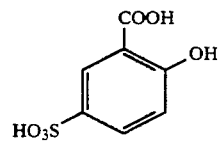

wherein R represents H or Cl.

2. 1-(2-((4-chlorophenyl)-methoxy)-2-(2,4-dichlorophenyl)-ethyl)-1H-imidazole 5-sulfosalicylic acid addition salt, a compound according to claim 1.

3. 1-(2-((2,4-dichlorophenyl)-2-(2,4-dichlorophenyl)-methoxy)-ethyl)-1H-imidazole 5-sulfosalicylic acid addition salt, a compound according to claim 1.

4. Pharmaceutical composition for topical use, characterized by containing, as the active ingredient an anti-mycotic effective amount of a compound according to claim 1, together with a pharmaceutically acceptable excipient, vehicle, solvent or diluent.

5. Pharmaceutical composition according to claim 4 in form of a cream, ointment, lotion, gel, milk, tincture, powder, ovuli, foam, vaginal capsule, or vaginal washing.

6. Pharmaceutical composition according to claim 4 wherein the active ingredient is an effective amount of a compound of claim 1 for use in the therapy of cutaneous mycosis.

7. A method of treatment of topical fungal infections by administering an antifungal effective amount of a compound of claim 1.

* * * * *